(12) United States Patent
Gering et al.

(10) Patent No.: US 7,620,227 B2
(45) Date of Patent: Nov. 17, 2009

(54) COMPUTER-AIDED DETECTION SYSTEM UTILIZING TEMPORAL ANALYSIS AS A PRECURSOR TO SPATIAL ANALYSIS

(75) Inventors: David Thomas Gering, Waukesha, WI (US); Gopal B. Avinash, New Berlin, WI (US); Sandeep N. Gupta, Hanover, MD (US)

(73) Assignee: General Electric Co., Schenectady, NY (US)

( * ) Notice: Subject to any disclaimer, the term of this patent is extended or adjusted under 35 U.S.C. 154(b) by 728 days.

(21) Appl. No.: 11/321,510

(22) Filed: Dec. 29, 2005

(65) Prior Publication Data

US 2007/0165920 A1   Jul. 19, 2007

(51) Int. Cl.
*G06K 9/00* (2006.01)
*A61B 5/05* (2006.01)

(52) U.S. Cl. .................. 382/128; 382/154; 600/400

(58) Field of Classification Search .......... 382/128, 382/129, 130, 131, 132, 133, 134, 154, 162, 382/168, 173, 181, 194, 199, 203, 224, 232, 382/240, 256, 274, 305, 312, 318; 600/410, 600/300, 408
See application file for complete search history.

(56) References Cited

U.S. PATENT DOCUMENTS

| | | | | |
|---|---|---|---|---|
| 5,235,510 A  * | 8/1993 | Yamada et al. | ............... | 600/300 |
| 6,317,617 B1 * | 11/2001 | Gilhuijs et al. | ............. | 600/408 |
| 6,438,403 B1 * | 8/2002 | Cline et al. | .................. | 600/410 |
| 7,251,374 B2 * | 7/2007 | Niemeyer | .................... | 382/240 |
| 7,391,893 B2 * | 6/2008 | Liang et al. | .................. | 382/128 |
| 2005/0074149 A1 * | 4/2005 | Niemeyer | .................... | 382/128 |
| 2005/0111716 A1 | 5/2005 | Collins et al. | | |
| 2005/0111718 A1 | 5/2005 | MacMahon et al. | | |

* cited by examiner

*Primary Examiner*—Seyed Azarian

(57) ABSTRACT

A computer-aided detection system for evaluating tissue based on a series of timed images acquired both before and after a contrast agent is administered performs a temporal analysis of the tissue and then a spatial analysis in which the tissue is categorized. After the temporal and spatial analysis is performed, the results can be displayed. The displayed results can include both tissue characterization results, underlying curves used to determine the characterization, and confidence data regarding how good the characterization is expected to be. The confidence data can be provided, for example, by using variations in color schemes, displaying numerical confidence levels, or providing graphical features such as piecewise linear models.

17 Claims, 9 Drawing Sheets

COMPUTER-AIDED DETECTION SYSTEM UTILIZING TEMPORAL ANALYSIS AS A PRECURSOR TO SPATIAL ANALYSIS

TECHNICAL FIELD

The present invention generally relates to computer-aided detection (CAD) in medical imagery and, in particular, relates to an improved method for providing computer-aided detection of lesions and tumors by analyzing dynamic properties in contrast enhanced medical images.

BACKGROUND OF THE INVENTION

Medical imaging technologies, such as Computed Tomography (CT), Positron Emission Tomography (PET), Single Photon Emission Computed Tomography (SPECT), and Magnetic Resonance Imaging (MRI) detect and record tissue responses in the presence of applied signals and/or injected or ingested substances, and generate visual representations indicative of such responses. This data can be analyzed to differentiate or monitor various types of tissue, and can be used to diagnose malignancies in the tissue.

In typical medical imaging techniques a volume of tissue is scanned within a region of anatomical interest. The acquired scan data can then be transformed into or reconstructed as a series of planar images or image "slices." Any given image slice comprises an array of volume elements or voxels, where each voxel corresponds to an imaging signal intensity within an incremental volume that may be defined in accordance with x, y, and z axes. At any particular time, the intensity of an imaging signal associated with a particular voxel depends upon the types of tissues within an anatomical region corresponding to the voxel.

In some imaging applications, a contrast agent is administered to the patient to selectively enhance the imaging properties of a selected tissue type. In these applications, the intensity of the imaging signal can help to differentiate healthy from malignant tissue. Furthermore, the response of the tissue with respect to time following contrast agent administration is also useful in evaluating tissue. Temporally varying or dynamic tissue dependent contrast agent uptake properties, for example, can be used to identify particular tissue types, and to differentiate malignant from benign tissues.

Gadolinium DPTA and other contrast agents are often used in conjunction with MRI processes to improve the distinction between types of soft tissue, and particularly to distinguish malignant versus benign breast tumors or lesions. Normal or healthy tissue typically exhibits a background signal intensity in the absence of a contrast agent, while abnormal or tumorous tissue exhibits either a reduced, increased, or substantially similar signal intensity relative to the background intensity. Thus, prior to contrast agent administration, abnormal tissue may or may not appear different from normal tissue.

When a contrast agent is applied, in general a lesion will exhibit one of many types of time-dependent contrast agent uptake behaviors. Within imaging data corresponding to a time series of scans, each type of contrast agent uptake behavior manifests as a corresponding type of dynamic imaging signal intensity profile or curve. Each type of dynamic intensity curve probabilistically corresponds to whether the lesion is benign or malignant.

The imaging data acquired both before and after the administration of the contrast agent can therefore be provided to a computer for computer-aided detection (CAD) of cancer and other malignancies. The CAD system receives the acquired images, and calculates a set of measurements or features in the region of interest. Based on the calculated data, the CAD system categorizes tissue in the region of interest and provides a display to a user, typically a radiologist. The display typically includes both an indicator of a potentially malignant area and also a numerical parameter or rating, such as a percentage enhancement of the brightness of the tissue in the selected area.

In practice, most CAD system displays are readily interpreted by users. That is, a displayed detection is either accepted as malignant or is easily dismissed as a false positive mark due to some observable artifact in the image. However, users may desire more information about the region that was marked. Since CAD systems typically base display decisions on computed numerical scores from a plurality of measurements, there is no current method for providing feedback to a radiologist regarding why a particular image region was marked or not.

Therefore, there is a need for providing data to users indicating the factors influencing a CAD system's determination about whether or not to mark a particular region as a detection.

BRIEF SUMMARY OF THE INVENTION

In one aspect, the present invention provides a method for computer-aided detection of a malignancy in a four-dimensional series of medical images, comprising the steps of accessing a series of three dimensional medical images of a region of interest over a period of time, at least one set in the series being taken before administration of a contrast agent and a plurality of sets taken after the administration of a contrast agent to produce a four dimensional image, characterizing each voxel in the four dimensional image as one of a plurality of tissue types based on a temporal analysis, and spatially segmenting each voxel in the four-dimensional image into tissue types based on the temporal characterization.

In another aspect, the invention provides a method for computer-aided detection of a malignancy in a four-dimension series of medical images comprising the steps of accessing a series of three dimensional medical images of a region of interest over a period of time, at least one set in the series being taken before administration of a contrast agent and a plurality of sets taken after the administration of a contrast agent to produce a four dimensional series of images, selecting a first scale space for processing the images and, for each of the images in the series, performing a temporal analysis of the voxels in the image to identify voxels of interest, performing a spatial analysis of the voxels in the image to identify voxels of interest and to segment the image into tissue types, and selecting a new scale space and repeating over a range of scale spaces.

In yet another aspect of the invention, a method for providing a display of a computer-aided detection of a malignancy in a four-dimensional series of medical images is provided, comprising the steps of accessing a series of three dimensional medical images of a region of interest over a period of time, at least one set in the series being taken before administration of a contrast agent and a plurality of sets taken after the administration of a contrast agent to produce a four dimensional series of images, performing a temporal analysis of the voxels in the image to identify voxels of interest and producing a graph of intensity over time at each voxel, performing a spatial analysis of the voxels in the image to identify voxels of interest and to segment the image into tissue types and associating a visual data indicator to each voxel as an indicator of the probability that a given voxel is tissue of a given type, and displaying both the graph of intensity over time and the visual indicator at each voxel.

In yet another aspect of the invention, a preliminary temporal analysis on a four-dimensional series of medical images can be performed and used in two ways: one, to select voxels for which detailed spatial and temporal analysis needs to be performed, thereby greatly speeding up the analysis; and two, by limiting the display of the results of the spatial and temporal analysis of voxels to those that meet certain criteria, thus improving the interpretability of the results.

These and other aspects of the invention will become apparent from the following description. In the description, reference is made to the accompanying drawings that form a part hereof, and in which there is shown a preferred embodiment of the invention. Such embodiment does not necessarily represent the full scope of the invention and reference is made therefore, to the claims herein for interpreting the scope of the invention.

DESCRIPTION OF THE PREFERRED EMBODIMENT

Figure 1:
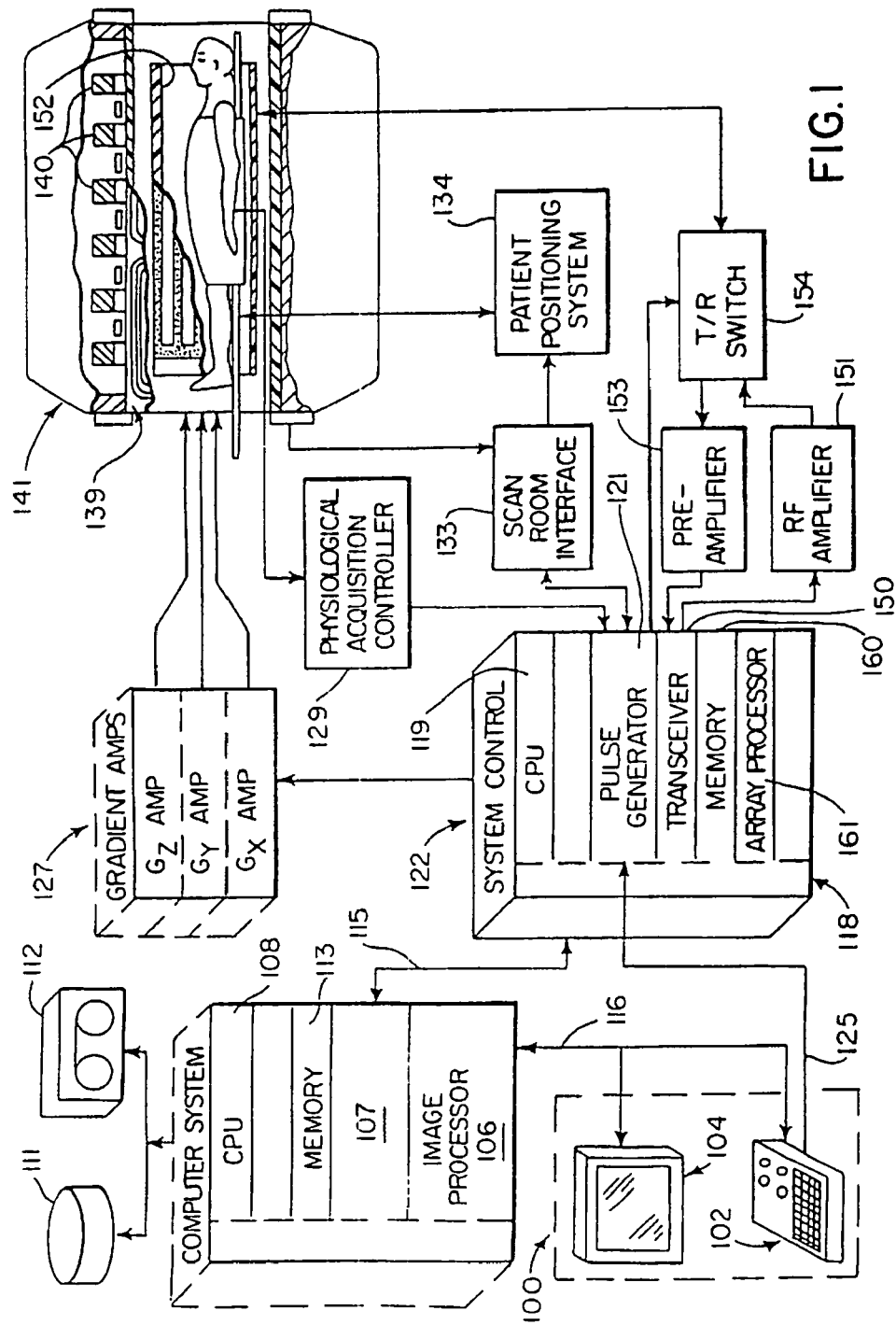
FIG. 1 is a block diagram of a magnetic resonance imaging system for acquiring images useful in the present invention.

Referring first to FIG. 1, there are shown the major components of a magnetic resonance imaging system (MRI) useful in acquiring images for the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of Gx, Gy and Gz amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

Although an MRI system is shown and described, it will be apparent that the images for the present invention could also be acquired using Computed Tomography (CT), Positron Emission Tomography (PET), Single Photon Emission Computed Tomography (SPECT), Ultrasound, or other imaging technologies.

Figure 2:
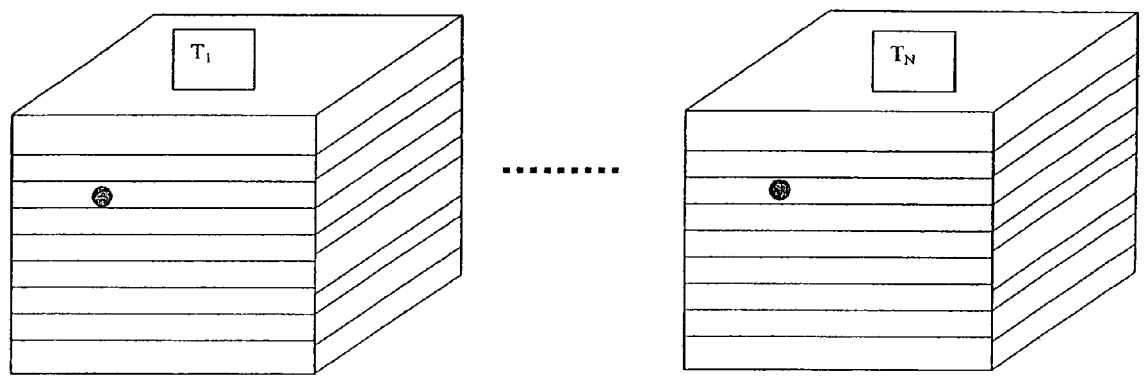
FIG. 2 is a block diagram of a time series of three dimensional medical images.

Referring now to FIG. 2, in the present invention, a four dimensional image data set is acquired using a medical imaging system of any of the types described above. The data set consists of a series of 3D volumes collected over time, here at time intervals interspersed between times $T_1$, and $T_n$. During the acquisition, images are acquired both before and after the administration of a contrast agent to allow for analysis of the reaction of the tissue to the contrast agent in a region of interest (ROI). Initially, therefore, at time $T_1$, one or more pre-contrast agent scans are performed to acquire a baseline image for comparison purposes. At some intermediate time between times $T_1$, and $T_n$ a contrast agent is administered. A series of 3D volumes are acquired at time intervals between $T_1$, and $T_n$, such that the reaction of tissue in a selected region of interest can be evaluated as the contrast agent is absorbed into the tissue.

When acquiring images as described with reference to FIG. 2, the level of contrast agent within vasculature associated with a lesion increases or decreases the imaging signal intensity soon after the contrast agent is administered. Depending upon the imaging protocol and lesion characteristics, tissue dependent contrast agent kinetics may subsequently give rise to a characteristic imaging signal intensity.

Figure 3A:
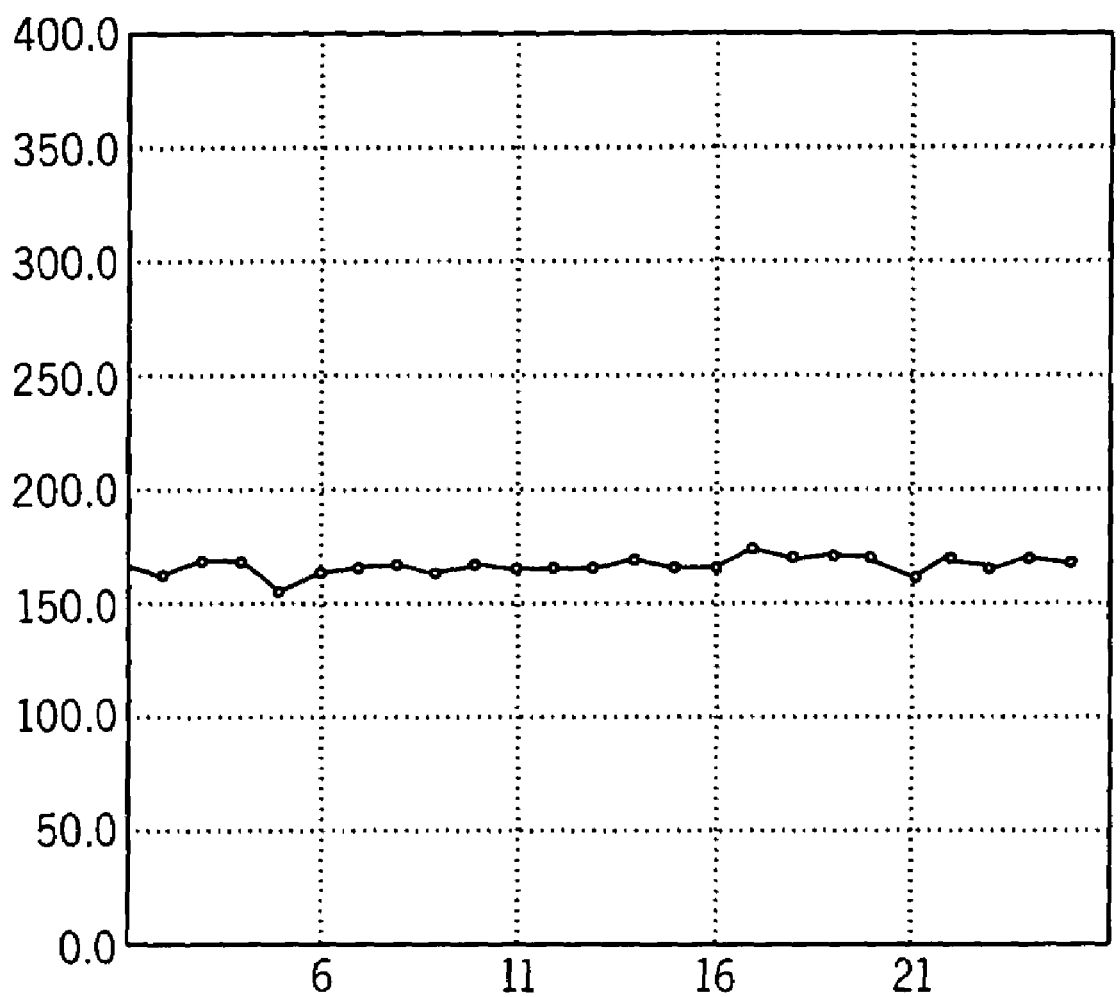
FIG. 3A is an intensity versus time curve characteristic of healthy breast tissue.
Figure 3B:
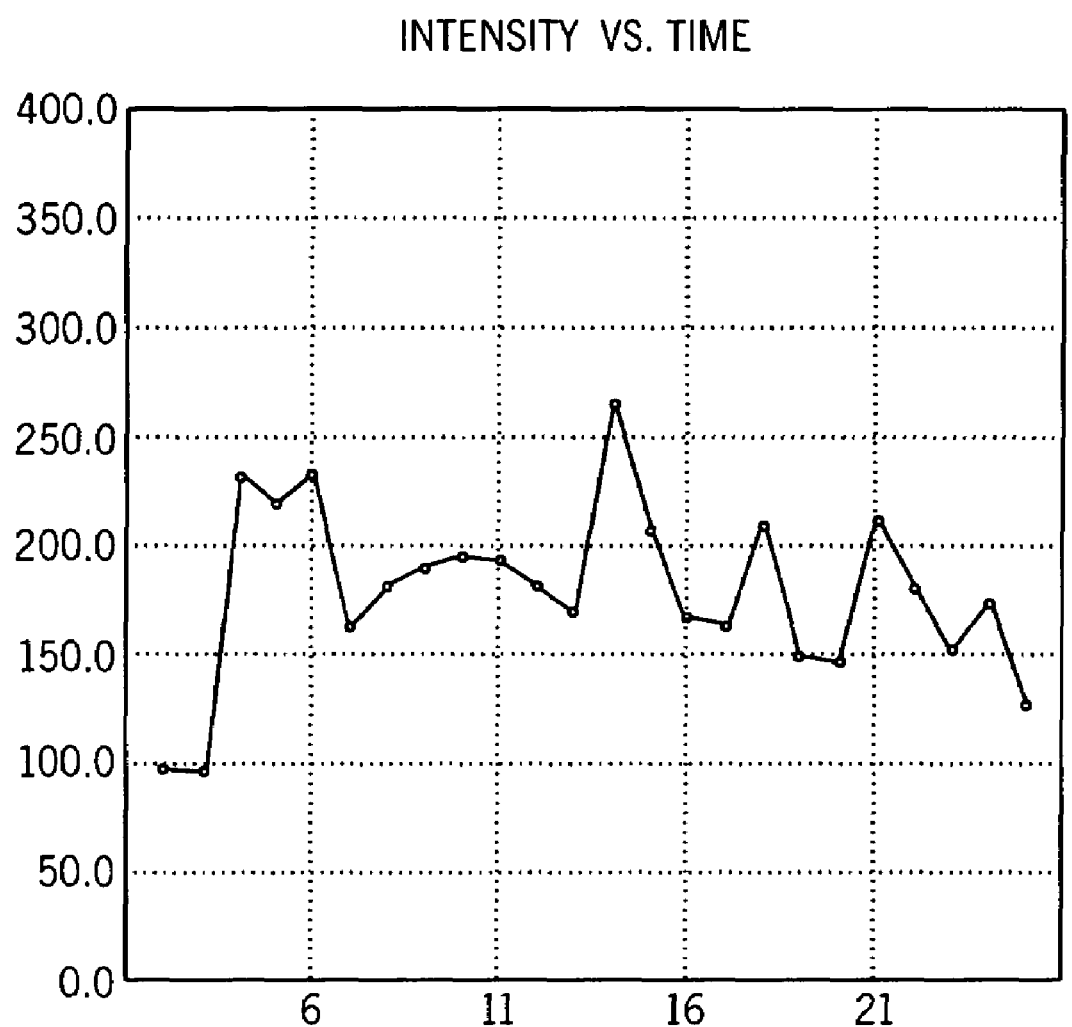
FIG. 3B is an intensity versus time curve characteristic of cardiac tissue.
Figure 3C:
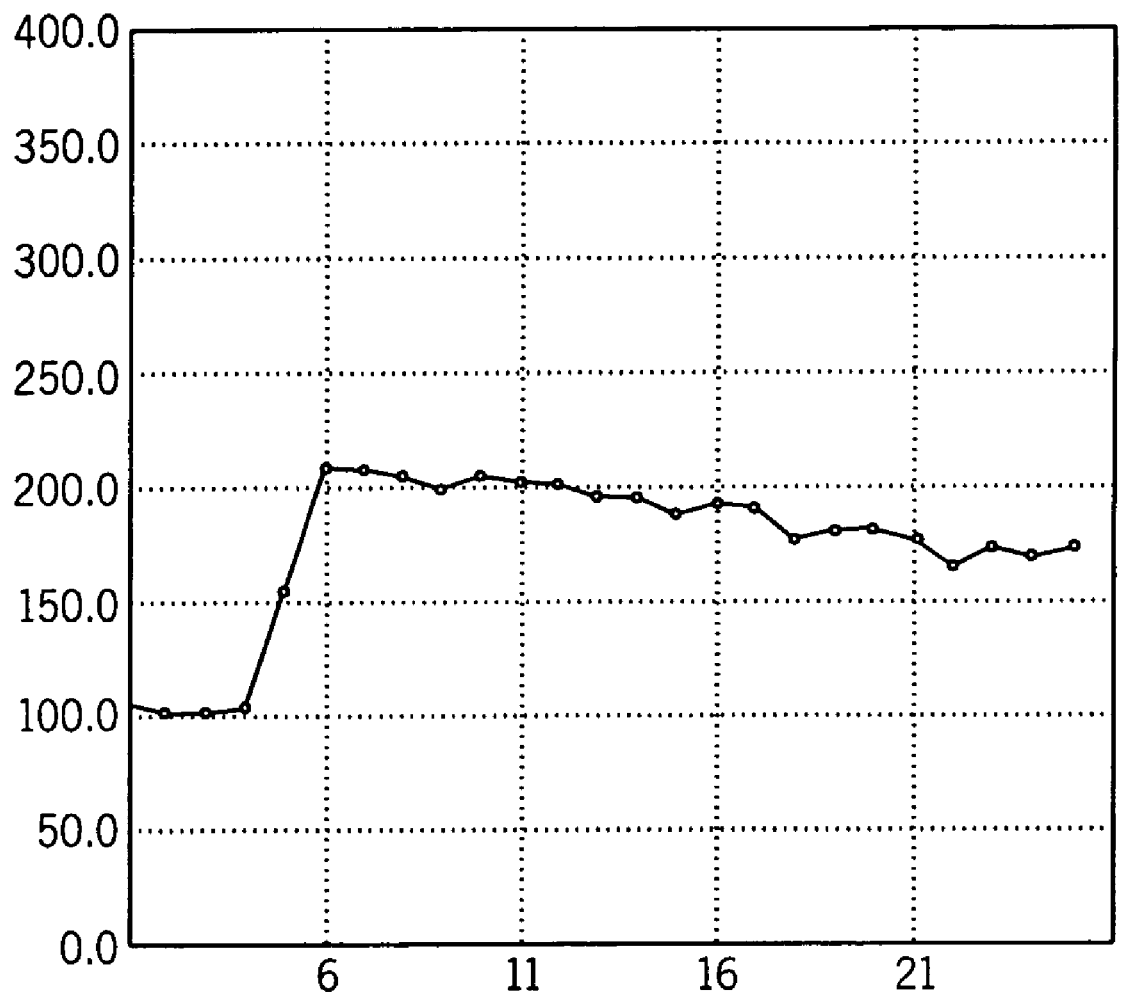
FIG. 3C is an intensity versus time curve characteristic of tumor tissue.

Referring now to FIGS. 3a-3c, due to these variations in reaction to a contrast agent over time, tissue can be characterized based on a comparison of the intensity versus time profile to known characteristics of tissue. As an example of breast MRI, the uptake curve for three different tissue samples are shown, illustrating the reactions of tissue types in terms of intensity versus time curves for a time period between time $T_1$ and time $T_n$. In the first sample of FIG. 3a, the variation in intensity is relatively constant with respect to time, resulting in a relatively flat profile. This profile is typically representative of healthy tissue. Referring now to FIG. 3b, here the intensity of the image at the voxel varies in an undulating fashion with respect to time, a response that is known to be characteristic of moving cardiac tissue. Referring now to FIG. 3c, the intensity of the image at a third tissue sample varies such that, prior to the application of the contrast agent, the intensity is at a first relatively low level, then rises to a relatively high peak level, and then plateaus. This reaction is characteristic of tumor tissue. The intensity versus time profile can therefore be used to characterize the tissue through analysis using a computer-aided detection or computer-aided diagnosis system.

Figure 4:
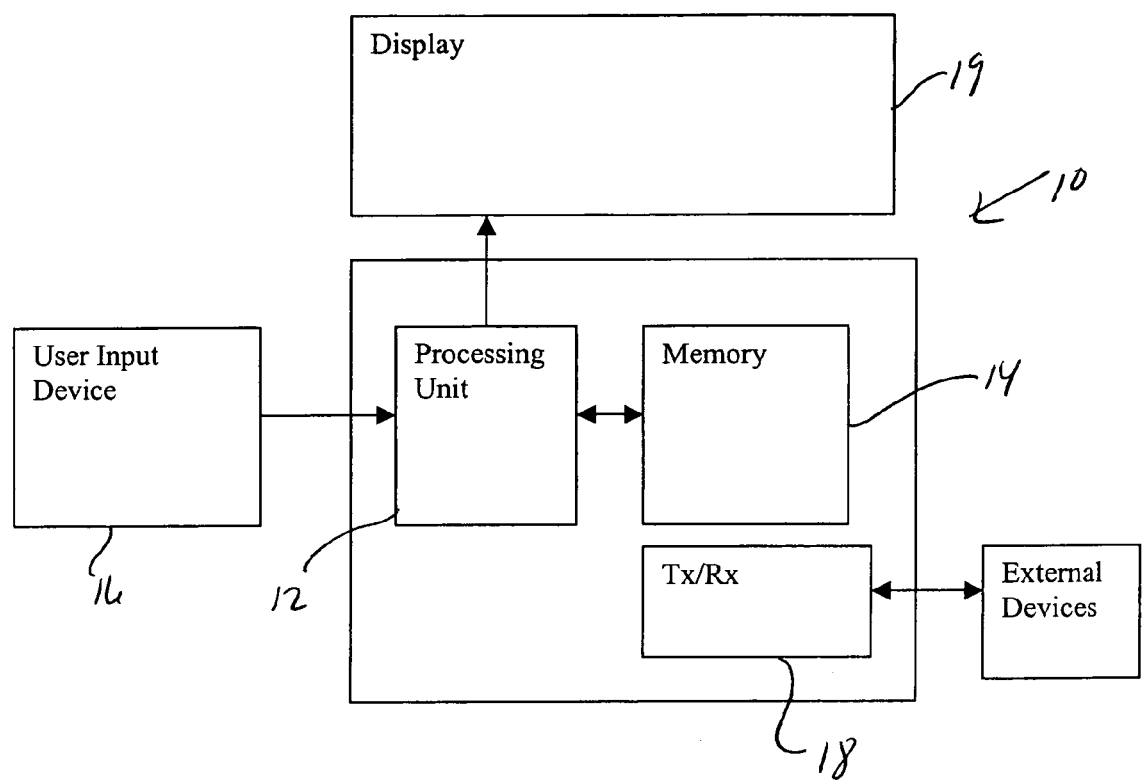
FIG. 4 is a block diagram of a computer-aided detection system of the present invention.

Referring now to FIG. 4, a block diagram of a computer-aided detection system 10 constructed in accordance with the present invention is shown. The computer-aided detection system comprises a processing unit 12, display 19, user input device 16, and memory component 14 or other machine-readable medium. The memory component 14 can be used both to store images, as described below, and computer code including software or algorithms for processing the images to provide computer-aided detection functions, as described below. The computer-aided detection system 10 can also include a communication device 18 for transmitting and receiving communications from external devices. The communication device can be any number of known devices, including network devices, modems, universal serial bus devices, or other types of ports. Although specific hardware devices can be provided for the computer-aided detection system, off the shelf personal computers are preferably used in the present invention.

Figure 5:
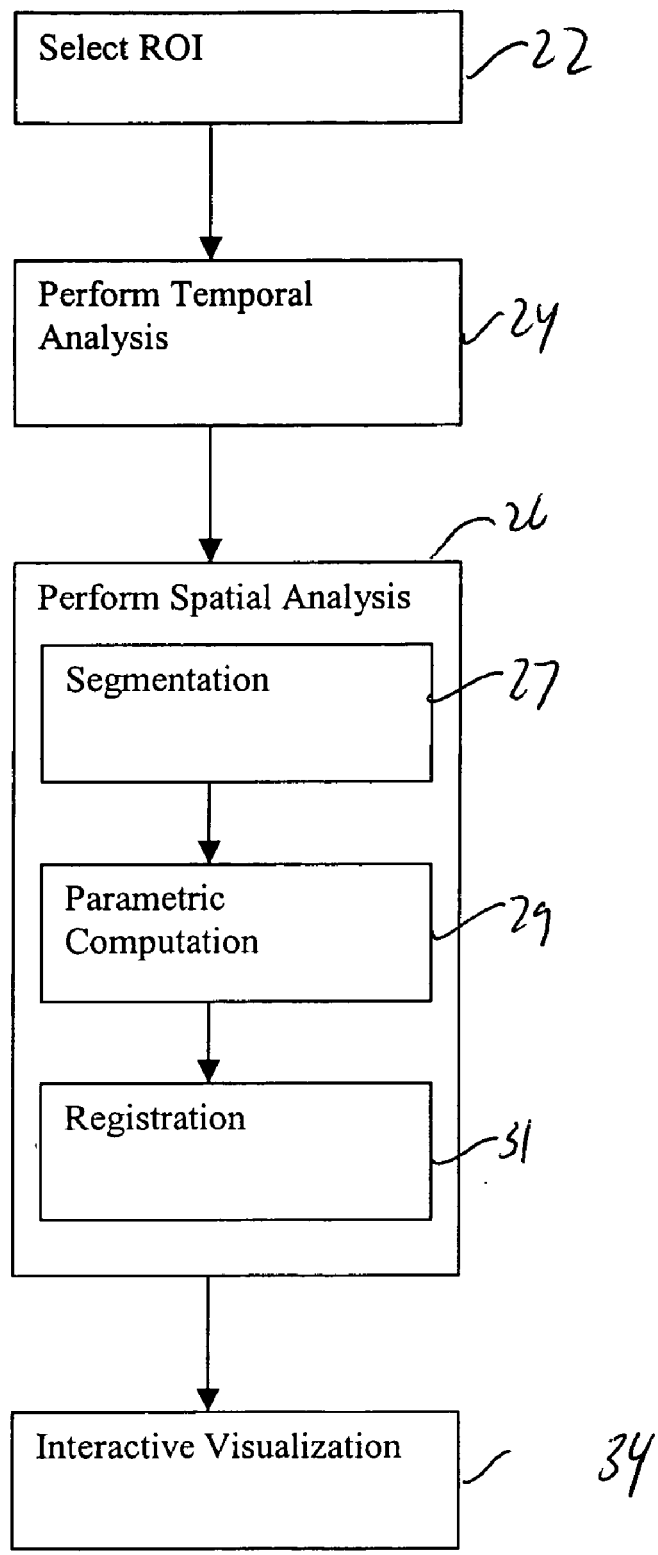
FIG. 5 is a flow chart illustrating a computer-aided detection algorithm for a first embodiment of the present invention.

Referring now FIG. 5, an algorithm useful in a first embodiment of a computer-aided detection system of the present invention is shown. After the data of FIG. 2 is acquired, it can be transmitted or otherwise transferred to the memory component 14 of the computer-aided detection system 10, or can be stored in a remote location accessible to the computer-aided detection system 10. After the four dimensional series of imaging data is provided to the computer system 10 in step 22, a region of interest is selected on the original acquired images. The specific region of interest (ROI) can be selected either spatially or temporally. To select the ROI spatially, a user can use the user input device 16, which can be, for example, a keyboard, mouse, joystick, or other device, to select boundaries on the original image either by drawing the boundary or by selecting the boundary using numerical coordinates. This selection can also be automated to separate, for example, body from background. To select the ROI temporally, the user can specify numerical threshold limits of interest, and the acquired can be filtered according to these limits. The quantity being limited could be a parameter whose computation time is far shorter than that of the full temporal analysis performed in step 24, as discussed below.

Referring still to FIG. 5, after the region of interest is selected, in step 24, a temporal analysis of the intensity profile of each voxel with respect to time is performed to characterize the tissue at the voxel. Characterization involves extracting a description of the curve by performing at least one of fitting parameters, searching for the presence or absence of various features, or curve fitting. When curve fitting, for example, the intensity versus time curve for each voxel can be compared to one or more characteristic profiles stored in the memory 14 of the computer-aided detection device 10. The comparison can involve fitting a piecewise-linear model using the method of minimized least squares, or fitting one or more parametric functions, or in other ways known in the art. Additionally, this analysis can further comprise categorizing the voxels with respect to at least one tissue type. A probability factor indicating the likelihood that the voxel is a particular type of tissue can be determined and associated with the voxel based on how closely the profile tracks the profile of a known type of tissue. Furthermore, a confidence factor can also be associated with each voxel.

Referring again to FIG. 5 after the temporal analysis is performed in step 24, a spatial analysis of the tissue in the region of interest is performed in step 26. Initially, in step 27, the image is segmented into predefined types of tissues. The segmentation can be performed using Bayesian probability analysis to select the maximum a posterior hypothesis (MAP) for each voxel. Bayesian analysis combines two components: the likelihood that the observed data was generated given the hypothesis of tissue type, and the probability of the hypothesis being true given what is known prior to observing the data. When the prior probabilities of all hypotheses are equal, then the method is equivalent to selecting the maximum likelihood hypothesis (ML). In embodiments that use Bayesian analysis, the computation of at least one of the prior probabilities and the likelihood probabilities are influenced by the results of the temporal analysis.

Spatial attributes can also be incorporated into a Bayesian analysis by fitting probability distributions to spatial features. This fitting can be accomplished by solving for the parameters of the probability distributions based on measurements made from training data. In the absence of training data, these distributions can be estimated from the image data using Parzen windows. When not only the parameters, but also the forms, of the probability distributions are not known a priori, then the non-parametric methods of nearest-neighbor classifiers and fuzzy classifiers can be applied. The spatial attributes being analyzed using these methods can include local and global features. A local attribute, for example, is the information associated with the voxels in the neighborhood of a given voxel. Markov random fields provide a probabilistic approach to modeling this neighborhood coherence. Other local attributes include, for example, image gradients and curvature. Other spatial attributes are more global in scope, such as the bias field present in MRI due to surface coil in-homogeneity. Expectation maximization is a probabilistic method for simultaneously segmenting the image and estimating the bias field. Other spatial attributes include measurements made on the segmentation thus far, such as the curvature, size, and thickness of structures, and the distance from structural boundaries. Probabilistic information computed locally within the image can be propagated for use by the analysis in remote areas of the image using probabilistic methods such as Bayesian belief propagation methods and other graphical models. Furthermore, prior information can be incorporated into Bayesian schemes by registering an anatomical atlas to the image data, which is essentially a voxel-by-voxel map of spatially varying prior probabilities. Shape models can also be fit to the image data and/or the segmentation to provide contextual information.

During segmentation, each of the voxels is categorized as a tissue type, and can be assigned, for example, a color associated with that type of tissue. In step 29, a parametric analysis or computation is performed. Here, a probability is determined for each voxel, and the assigned color can be varied based on the probability that the tissue actually is of a selected type. For example, the color can be varied based on the percent likelihood that the segmentation classification is correct. As another example, the assigned color can be varied based on the most probable tissue type.

Finally, upon completion of the segmentation 27 and parametric calculation 29, the images acquired between times $T_1$ and $T_n$, can be registered or aligned to account for movement during the acquisition and to verify the position of each image, as shown in step 31. This procedure can be performed using any number of known image registration methods. While shown here following steps 27 and 29, the registration can be performed at various stages of the process.

Figure 6:
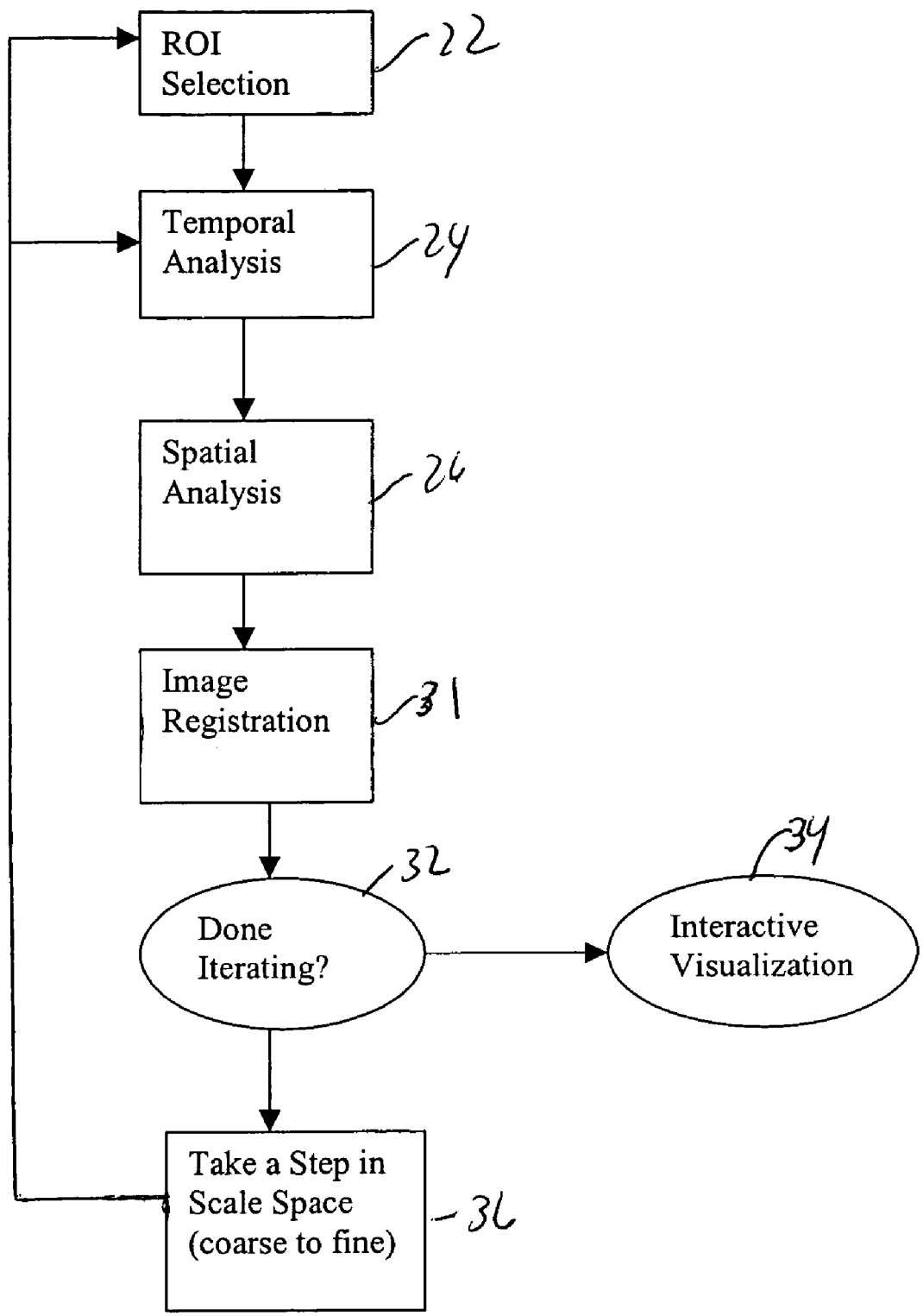
FIG. 6 is a flow chart illustrating a computer-aided detection algorithm for an alternate embodiment of the present invention.

Referring now to FIG. 6, in a second embodiment, the computer-aided detection system 10 processes the data through a series of iterations in which the scale space, e.g. the number of voxels evaluated in a given image, is varied between a minimum coarse level (as low as a 1×1) and a maximum fine level (such as 256×256). Iterations can be made at predetermined steps in scaled space. Here, an initial scale space and iteration level are selected prior to processing. After these parameters are selected, a specific region of interest (ROI) is selected either spatially or temporally, as described above with reference to step 22, and the image in the selected region of interest is then evaluated.

After a region of interest is selected, the temporal analysis 24 and spatial analysis 26 are performed as described above for the selected scale space. Then, in step 32, a determination is made as to whether the analysis has been performed at all the predetermined scale space steps. If the image has been analyzed at all the predetermined scale space steps, the process is stopped, and the images can be visualized in step 34. However, if additional scale space analysis is required in step 36, the scale space is adjusted to a finer fine level (i.e. the number of voxels in the image is increased such that each voxel represents a smaller volume). After the scale space is adjusted, a new region of interest can be selected based on the results at the previous scale space level, or the process can proceed to temporal analysis in step 24. In embodiments where the region of interest is altered between scales, the results of the previous scale space level are applied toward focusing the subsequent computations on the most relevant portions of the image. By changing the scale space as the analysis proceeds, the speed of processing is increased allowing the diagnosis to be completed in a significantly reduced period of time. As described above, as one step of the process the images are preferably registered using known algorithms. The registration step benefits from an accurate segmentation step, and the segmentation step benefits from an accurate registration step. For this reason, iteration is helpful, but it is also time-consuming, thus the motivation for changing the scale during iteration. While shown here following steps 26, the registration can be performed at various stages of the process.

Figure 7:
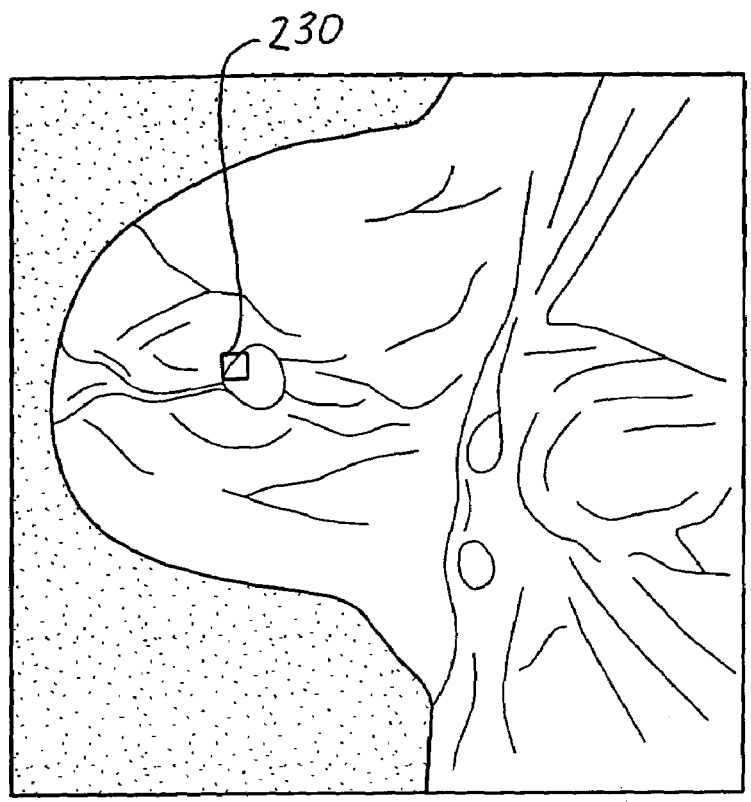
FIG. 7 is an original image illustrating the selection of a region of interest.
Figure 8:
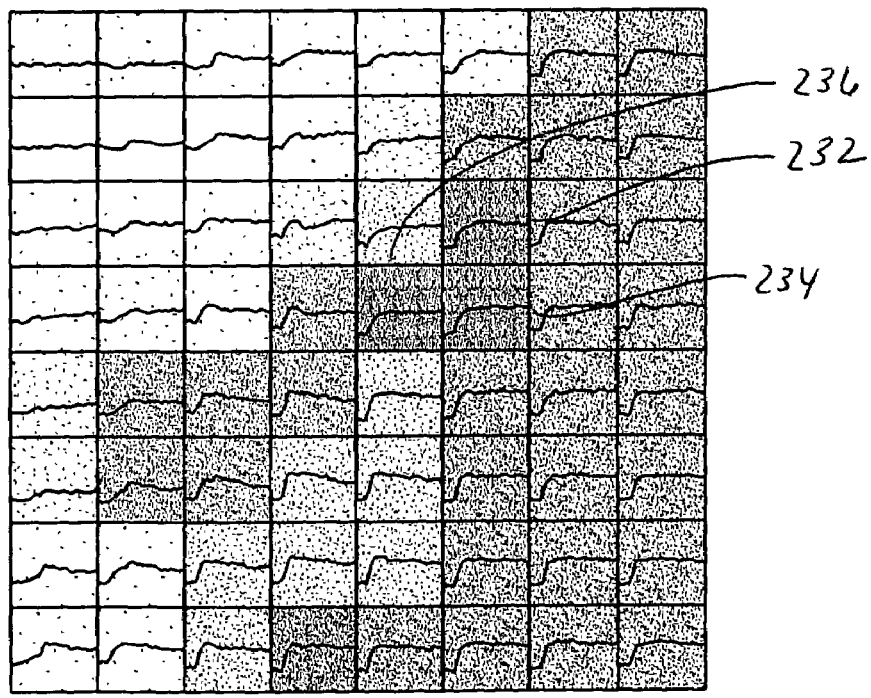
FIG. 8 is a display illustrating segmented voxels and associated intensity versus time curves.

Referring now to FIG. 7 and FIG. 8, when using either of the algorithms described above, the results can be visualized. Referring first to FIG. 7, a displayed image of a breast analyzed in accordance with the process described above is shown, with a selected region of interest delineated by the box 230. Referring now also to FIG. 8, for each voxel in the region of interest 230, a visual parameter can be assigned based on the segmentation of the spatial analysis described above. For example, malignant tissue can be assigned a first color and healthy tissue another. As shown here, for example, the darker segments in the center of the block of FIG. 8 and delineated as 232, 234, and 236 are likely tumor, whereas the light surrounding blocks are likely healthy tissue.

The parametric analysis provides variations illustrating how close the tissue is to being either healthy or malignant by, for example, shading the color between the possible options based on the probability analysis. For example, a single voxel may have a 30% probability that it is a healthy breast tissue and a 50% probability that it is a tumor tissue and a 20% probability that it is a heart tissue. These probabilities can be reflected in the parametric coloring.

Referring still to FIG. 7, to provide additional information to the medical personnel performing the analysis, the intensity over time curves for each of the voxels can also be displayed. In addition to the curve, the display can optionally include an indication of goodness of fit to a model. These displays can include, for example, piecewise linear models, graphs of parametric functions, text revealing numerical parameters, graphical features such as shading, and other indicators. The time versus intensity curves can be overlaid on the original scan, or on a purely segmented view, or on a parametric view including coloring such as a percent enhancement. Various other parameters can also be provided. The practitioner, moreover, can interactively select the level and types of data to be visualized on the display 19 through the user input device 16.

The present invention therefore provides an array of information to a medical practitioner rather than a single computed detection parameter. In addition to providing an analysis of which tissue is tumor tissue and which is healthy, the present invention provides graphic displays of variations between these levels. Furthermore, to allow medical practitioners to verify the analysis, the time verses intensity curve and other parametric data can also be provided, such that the practitioner can more easily verify the results of the computer-aided detection.

The parametric coloring that indicates tissue classification, or the probability of membership in a given tissue class, can be useful in rendering 2-D and 3-D displays. In 2-D displays, the parameters can be used to assign colors to each voxel to overlay on grayscale anatomical images. In 3-D surface renderings, the parameters can be used to assign colors to surface patches, where the surfaces envelope the anatomical structures identified during the segmentation process. In 3-D volume rendering, the parameters can be used to assign colors and/or opacity attributes to voxels to provide the information required for ray-tracing.

It should be understood that the methods and apparatuses described above are only exemplary and do not limit the scope of the invention, and that various modifications could be made by those skilled in the art that would fall under the scope of the invention.

To apprise the public of the scope of this invention, the following claims are made:

1. A method for computer-aided detection in a four-dimensional series of medical images, the method comprising the following steps:
   (a) accessing from a memory a series of three dimensional medical images of a region of interest over a period of time, at least one set in the series being taken before administration of a contrast agent and a plurality of sets taken after the administration of a contrast agent to produce a four dimensional image;
   (b) performing a temporal analysis using a processing unit to characterize each voxel in the four dimensional image, wherein the performing a temporal analysis step includes the steps of accessing at least one stored curve representative of a known tissue type, comparing the intensity over time at the voxel to the at least one curve, and classifying tissue based on the probability that the tissue at the voxel is the type represented by the curve; and
   (c) performing a spatial analysis influenced by the temporal characterizations using the processing unit to segment the voxels into tissue types.

2. The method as recited in claim 1, further comprising the steps of identifying voxels of interest based on the analysis in step (b) and using the identified voxels of interest in step (c) to perform the spatial analysis.

3. The method as recited in claim 1, further comprising the step of registering the images in the series of three-dimensional images.

4. The method as recited in claim 1, wherein step (b) comprises applying a curve-fitting analysis.

5. The method as recited in claim 1, wherein step (c) comprises determining a probability that each voxel is of the selected tissue type.

6. The method as recited in claim 5, wherein the probability is determined based on a method including at least one of a Bayesian maximum a posteriori analysis, a maximum likelihood analysis, an expectation maximization, a Markov model, a nearest-neighbor classifier, a fuzzy classifier, a classifier based on Parzen window estimation, and a Bayesian belief propagation network.

7. The method as recited in claim 1, wherein the medical images are acquired through at least one of an MRI, a CT, a PET, a SPECT, and an ultrasound scan.

8. The method as recited in claim 1, further comprising the step of providing a user interface and allowing a user to select a region of interest by selecting at least one of a temporal parameter and a spatial region.

9. The method as recited in claim 1, wherein step (c) further comprises the step of using a spatial attribute including at least one of an image gradient, a curvature, a size of segmented structures, a distance to a segmented boundary, a thickness of segmented structures, a bias field, a neighborhood coherence model, a registered anatomical model, and a fitted shape model to segment the voxels.

10. A method for computer-aided detection in a four-dimensional series of medical images, the method comprising the following steps:
   (a) accessing from a memory a series of three dimensional medical images of a region of interest over a period of time, at least one set in the series being taken before administration of a contrast agent and a plurality of sets taken after the administration of a contrast agent to produce a four dimensional image;
   (b) performing a temporal analysis using a processing unit to characterize each voxel in the four dimensional image;
   (c) performing a spatial analysis influenced by the temporal characterizations using the processing unit to segment the voxels into tissue types, wherein the performing a spatial analysis step further comprises assigning a visual designator to each voxel based on at least one of the tissue type and a probability of belonging to a given tissue type.

11. The method as recited in claim 10, further comprising the step of assigning a color as the visual designator.

12. The method as recited in claim 11, further comprising the step of displaying the visual designator in at least one of a 2-D image, a 3-D surface rendering, a 3-D volume rendering, and a graph of intensity over time at each voxel.

13. The method as recited in claim 12, further comprising the steps of identifying voxels of interest in at least one of the analyses of step (b) and step (c) and using the identified voxels of interest to limit the display to at least one selected tissue type.

14. A method for computer-aided detection in a four-dimensional series of medical images, the method comprising the following steps:
   (a) accessing from a memory a series of three dimensional medical images of a region of interest over a period of time, at least one set in the series being taken before administration of a contrast agent and a plurality of sets taken after the administration of a contrast agent to produce a four dimensional image;
   (b) selecting a first scale space for processing the images and, for each of the images in the series;
   (c) performing a temporal analysis using a processing unit to characterize each voxel in the four dimensional image
   (d) performing a spatial analysis based on the temporal characterization using a processing unit to segment the voxels into at least one tissue type;
   (e) selecting a new scale space and repeating steps (c-d) over a range of scale spaces, and
   further comprising the steps of identifying voxels of interest based on the analysis in steps (c) and (d) to perform at least one of the steps of localizing the spatial analysis in step (d), adjusting the region of interest for the next scale space level, and limiting a display to at least one selected tissue type.

15. The method as recited in claim 14, further comprising the step of registering the images in the series of three-dimensional images.

16. The method as recited in claim 14, further comprising the steps of associating a visual designator based on at least one of a tissue type and a probability of belonging to a given tissue type and displaying the visual designator in at least one of a 2-D image, a 3-D surface rendering, a 3-D volume rendering, and a graph of intensity over time at each voxel.

17. A method of computer-aided detection in a four-dimensional series of medical images, the method comprising the following steps:
   (a) accessing from a memory a series of three dimensional medical images of a region of interest over a period of time, at least one set in the series being taken before administration of a contrast agent and a plurality of sets taken after the administration of a contrast agent to produce a four dimensional image;
   (b) selecting a first scale space for processing the images and, for each of the images in the series;
   (c) performing a temporal analysis using a processing unit to characterize each voxel in the four dimensional image;

(d) performing a spatial analysis based on the temporal characterization using the processing unit to segment the voxels into at least one tissue type; and
(e) selecting a new scale space and repeating steps (c-d) over a range of scale spaces;
wherein the step of performing a temporal analysis comprises applying a curve-fitting analysis by accessing at least one stored curve representative of a known tissue type, comparing the intensity over time at the voxel to the at least one curve, and classifying tissue based on the probability that the tissue at the voxel is the type represented by the curve.

* * * * *

UNITED STATES PATENT AND TRADEMARK OFFICE
CERTIFICATE OF CORRECTION

PATENT NO. : 7,620,227 B2
APPLICATION NO. : 11/321510
DATED : November 17, 2009
INVENTOR(S) : Gering et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 993 days.

Signed and Sealed this

Twenty-sixth Day of October, 2010

David J. Kappos
*Director of the United States Patent and Trademark Office*